US011464741B2

(12) United States Patent
Davis et al.

(10) Patent No.: US 11,464,741 B2
(45) Date of Patent: Oct. 11, 2022

(54) SPRAY DRIED COMPOSITIONS HAVING DIFFERENT DISSOLUTION PROFILES AND PROCESSES FOR THEIR PREPARATION (71) Applicant: SpecGX LLC, Webster Groves, MO (US)

(72) Inventors: Joseph M. Davis, Hazelwood, MO (US); Robert C. Cuca, Hazelwood, MO (US); Edward J. Beasley, Hazelwood, MO (US)

(73) Assignee: SpecGX LLC, Webster Groves, MO (US)

( * ) Notice: Subject to any disclaimer, the term of this patent is extended or adjusted under 35 U.S.C. 154(b) by 200 days.

(21) Appl. No.: 14/722,541

(22) Filed: May 27, 2015

(65) Prior Publication Data
US 2015/0359743 A1 Dec. 17, 2015

Related U.S. Application Data (60) Provisional application No. 62/010,691, filed on Jun. 11, 2014.

(51) Int. Cl.
A61K 31/167 (2006.01)
A61K 9/16 (2006.01)
A61K 9/20 (2006.01)

(52) U.S. Cl.
CPC .......... A61K 9/1617 (2013.01); A61K 9/1623 (2013.01); A61K 9/1635 (2013.01); A61K 9/1652 (2013.01); A61K 9/1682 (2013.01); A61K 9/2013 (2013.01); A61K 9/2018 (2013.01); A61K 9/2027 (2013.01); A61K 9/2054 (2013.01); A61K 9/2059 (2013.01); A61K 31/167 (2013.01)

(58) Field of Classification Search
CPC .. A61K 31/167; A61K 9/1617; A61K 9/1623; A61K 9/1635; A61K 9/1652; A61K 9/1682; A61K 9/2013; A61K 9/2018; A61K 9/2027; A61K 9/2054; A61K 9/2059
USPC ........................................................ 514/630
See application file for complete search history.

(56) References Cited

U.S. PATENT DOCUMENTS

| 4,661,521 A | 4/1987 | Salpekar | |
| 4,710,519 A * | 12/1987 | Finnan | A61K 31/165 |
| | | | 424/489 |
| 4,904,477 A | 2/1990 | Ho | |
| 5,785,976 A | 7/1998 | Westesen | |
| 5,858,409 A | 1/1999 | Karetny | |
| 5,876,759 A * | 3/1999 | Gowan, Jr. | A61K 9/2081 |
| | | | 424/470 |
| 6,074,670 A | 6/2000 | Stamm | |
| 6,488,954 B1 | 12/2002 | Yoon | |
| 6,607,750 B2 * | 8/2003 | Upadhyay | A61K 9/2095 |
| | | | 424/464 |
| 6,696,084 B2 | 2/2004 | Pace | |
| 8,945,626 B2 | 2/2015 | Elphick | |
| 2003/0161879 A1 | 8/2003 | Ohmori et al. | |
| 2006/0062810 A1 | 3/2006 | Woo | |
| 2006/0140991 A1 | 6/2006 | Makino | |
| 2006/0292214 A1 | 12/2006 | Jenkins | |
| 2008/0003297 A1 * | 1/2008 | Yang | A61K 9/1617 |
| | | | 424/499 |
| 2008/0014228 A1 * | 1/2008 | Darmuzey | A61K 9/2054 |
| | | | 424/401 |
| 2008/0026063 A1 | 1/2008 | Ueda | |
| 2010/0068282 A1 | 3/2010 | Elphick | |
| 2010/0286100 A1 | 11/2010 | First | |
| 2011/0212173 A1 * | 9/2011 | Young | A61K 9/286 |
| | | | 424/468 |

FOREIGN PATENT DOCUMENTS

| JP | 2002-502813 | 8/2000 |
| JP | 2001-072578 | 3/2001 |
| JP | 2009-524665 | 9/2008 |
| WO | 95/58648 A1 | 12/1998 |
| WO | 1998058648 | 12/1998 |
| WO | 99/39700 | 8/1999 |
| WO | 00/50007 A1 | 8/2000 |
| WO | 2000050007 | 8/2000 |
| WO | 00/72827 A2 | 12/2000 |
| WO | 01/12155 A1 | 2/2001 |
| WO | 0112155 A1 | 2/2001 |
| WO | 2006-035900 | 6/2006 |
| WO | 2006082536 | 8/2006 |
| WO | 2007-089490 | 9/2007 |
| WO | 2010132095 | 11/2010 |

OTHER PUBLICATIONS

Kumar et al., Self-Emulsifying Drug Delivery Systems (SEDDS) for Oral Delivery of Lipid Based Formulations—A Review, International Journal of Pharmacy and Biological Sciences, 2012, pp. 42-53, vol. 2, Issue 2.
Lopez et al., Fast Dissolving Tablets—A Potential Drug Delivery System, Pharmatutor, downloaded May 26, 2015 (http://www.pharmatutor.org/articles/fast-dissolving-tablets-potential-drug-delivery-system).
International Search Report and Written Opinion dated Aug. 14, 2015 from related International application No. PCT/US15/32603, 9 pages.
Office action dated Jul. 11, 2018 from related Australian Application No. 2015275098, 4 pgs.
Notice of Acceptance dated Nov. 23, 2018 from related Australian Application No. 2015275098, 3 pgs.
Office action dated Dec. 4, 2018 from related Japanese Application No. 2016-569043, 7 pgs.
Japanese Publication for Opposition No. 51-011077 (no English language counterpart could be located).
European Search Report dated Dec. 8, 2017 from related EP Application No. 15807576.2, 1 pp.

(Continued)

Primary Examiner — Jared Barsky (57) ABSTRACT

The present disclosure provides compositions having different dissolution profiles. In particular, the compositions are formulated by adjusting the types and/or amounts of excipients and/or surfactants, and the compositions are prepared by spray drying processes.

1 Claim, 4 Drawing Sheets (56) References Cited

OTHER PUBLICATIONS

Office action dated Jan. 2, 2020 from related Mexican Application No. MX/a/2016/015528, 3 pages.
Office action dated Jun. 10, 2019 from related Japanese Application No. 2016-569073, 4 pages.
Examination Report dated Dec. 16, 2019 from related European Application No. 15 807 576.2, 5 pp.
"Aulton's Pharmaceutics, The design and manufacture of medicines", 2007, Elsevier Limited, pp. 434, 435 and 448.
Office action dated Jul. 24, 2020 from related Mexican Application No. MX/a/2016-015528, 4 pp.
Office action dated Dec. 15, 2020 from related Mexican Application No. MX/a/2016-015528, 4 pp.
Notice of Allowability in EP 3154528 A1 dated Oct. 14, 2021, 2 pages.

\* cited by examiner

SPRAY DRIED COMPOSITIONS HAVING DIFFERENT DISSOLUTION PROFILES AND PROCESSES FOR THEIR PREPARATION

CROSS-REFERENCE TO RELATED APPLICATIONS

This application claims the priority of U.S. Provisional Application Ser. No. 62/010,691, filed Jun. 11, 2014, which is hereby incorporated by reference in its entirety.

FIELD

The present disclosure relates to compositions having different dissolution profiles. In particular, the present disclosure relates to means for formulating the compositions and means for preparing the composition.

BACKGROUND

Dispersibility or dissolution is an important property of pharmaceutical compositions. For example, some compositions are fast dissolve or immediate release, and other composition provide extended dissolution. A variety of strategies have been used to modify the dissolution rates of pharmaceutical compositions. Such attempts have included changing the type and/or amounts of disintegrants, binders, or inactive fillers and/or coating the compositions with a variety of materials. Many of these attempts, however, require multiple processing steps which may include blending, granulating, compacting, milling, coating, and so forth. What is needed, therefore, is a simple process for preparing pharmaceutical composition having different dissolution profiles that does not require multiple processing steps.

SUMMARY

Among the various aspects of the present disclosure is the provision of a solid pharmaceutical composition, wherein the composition comprises at least one pharmaceutically active ingredient (API) having low aqueous solubility, a surfactant system comprising at least one nonionic surfactant, at least one zwitterionic surfactant, or a combination thereof, and at least one excipient other than a cellulose ether.

Another aspect of the present disclosure encompasses a process for preparing a plurality of spray dried particles. The process comprises forming an aqueous slurry by mixing into water i) at least one excipient, ii) at least one pharmaceutically active ingredient (API) having low aqueous solubility, and iii) a surfactant system comprising at least one nonionic surfactant, at least one zwitterionic surfactant, or a combination thereof; and spray drying the aqueous slurry to form the plurality of spray dried particles.

Other aspects and iterations of the disclosure are detailed below.

DETAILED DESCRIPTION

The present disclosure provides pharmaceutical compositions having different dissolution profiles which are formulated by adjusting the types and/or amounts of various excipients and including a surfactant system comprising at least one nonionic surfactant, at least one zwitterionic surfactant, or a combination thereof. The pharmaceutical compositions disclosed herein generally comprise active ingredients having low aqueous solubility, and the compositions are prepared using spray drying technology. Surprisingly, it was found that compositions comprising surfactant systems having high hydrophile-lipophile balance (HLB) values (i.e., more hydrophilic) exhibited delayed or extended rates of release of the active ingredients. In contrast, compositions comprising surfactant systems having low HLB values exhibited rapid or immediate rates of dissolution. Also provided herein are processes for preparing the pharmaceutical compositions disclosed herein.

(I) Compositions

One aspect of the present disclosure is a composition comprising at least one pharmaceutically active ingredient (API) having low aqueous solubility, a surfactant system comprising at least one nonionic surfactant, at least one zwitterionic surfactant, or a combination thereof, and at least one excipient.

(a) API

The composition disclosed herein comprises at least one API having low aqueous solubility (or stated another way, an API that is poorly soluble in water). The solubility of a compound is generally defined as the maximum concentration of a substance (i.e., a solute) that may completely dissolve in a given solvent at a given temperature and pressure. The United States Pharmacopeia (USP) generally expresses solubility in terms of the volume of solvent required to dissolve 1 gram of the solute at a specified temperature. For example, the USP defines a "sparingly soluble" API as one that requires from 30 to 100 parts of solvent to dissolve 1 part solute, a "slightly soluble" API as one that requires from 100 to 1000 parts of solvent to dissolve 1 part solute, a "very slightly soluble" API as one that requires from 1000 to 10,000 parts of solvent to dissolve 1 part solute, and a "practically insoluble" API as one that requires more than 10,000 parts of solvent to dissolve 1 part solute. As used herein, an API having "low aqueous solubility" refers to an API that meets the USP definition of "sparingly soluble," "slightly soluble," "very slightly soluble," or "practically insoluble."

A variety of APIs with low aqueous solubility may be included in the composition. Suitable APIs include, without limit, acetaminophen, nonsteroidal anti-inflammatory drugs (NSAIDs) such as ibuprofen, naproxen, diclofenac, flurbiprofen, ketoprofen, piroxicam, indomethacin, sulindac, tolmetin, meclofenamate, mefenamic acid, etodolac, ketorolac, or bromfenac; COX-2 inhibitors such as celecoxib or rofecoxib; opioid analgesics such as hydrocodone, hydromorphone, levorphanol, oxycodone, oxymorphone, codeine, morphine, alfentanil, fentanyl, meperidine, or sufentanil; diphenylheptanes such as levomethadyl, methadone, or propoxyphene; anilidopiperidines such as remifentanil; anxiolytic agents such as diazepam, alprazolam, chlordiazepoxide, clonazepam, halazepam, lorazepam, oxazepam, or clorazepate; selective serotonin reuptake inhibitors such as sertraline, paroxetine, fluoxetine, fluvoxamine, citalopram, venlafaxine, or nefazodone; tricyclic anti-depressants such as amitriptyline, doxepin, nortriptyline, imipramine, trimipramine, amoxapine, desipramine, protriptyline, clomipramine, mirtazapine, or maprotiline; anti-depressants such as trazodone, buspirone and bupropion; antipsychotic agents such as chlorpromazine, prochlorperazine, trifluoperazine, promethazine, promazine, thioridazine, mesoridazine, perphenazine, acetophenazine, clozapine, fluphenazine, chlorprothixene, thiothixene, haloperidol, droperidol, molindone, loxapine, risperidone, pimozide, or domepezil; attention deficit disorder and attention deficit hyperactivity disorder agents such as methylphenidate or pemoline; anti-migraine agents such as zolmitriptan, naratriptan, sumatriptan, rizatriptan, methysergide, ergot alkaloids, or isometheptene; cardiovascular agents such as angiotensin converting enzyme (ACE) inhibitors, diuretics, pre- and afterload reducers; cardiac glycosides such as digoxin or digitoxin; inotropes such as amrinone or milrinone; calcium channel blockers such as verapamil, nifedipine, nicardipene, felodipine, isradipine, nimodipine, bepridil, amlodipine, or diltiazem; beta-blockers such as pindolol, propafenone, propranolol, esmolol, sotalol and acebutolol; antiarrhythmics such as moricizine, ibutilide, procainamide, quinidine, disopyramide, lidocaine, phenytoin, tocainide, mexiletine, flecainide, encainide, bretylium, or amiodarone; cardioprotective agents such as dexrazoxane or leucovorin; peripheral vascular dilators such as cyclandelate, isoxsuprine, or papaverine; antihyperlipidemic agents including HMG-CoA reductase inhibitors such as atorastatin, simvastatin, pravastatin, lovastatin, or cerivastatin sodium, and other lipid-lowering agents such as clofibrate, fenofibrate, gemfibrozil, or tacrine; antimetabolic agents such as methotrexate, fluorouracil, floxuridine, cytarabine, mercaptopurine, or fludarabine phosphate; immunosuppressive agents such as 6-thioguanine, 6-aza-guanine, azathiopurine, cyclosporin, or methotrexate; antiarthritic agents such as hydroxychloroquine, gold-based compounds such as auranofin, aurothioglucose, or gold thiomalate; respiratory drugs such as theophylline, oxytriphylline, aminophylline, or other xanthine derivatives; leukotriene inhibitors such as zafirlukast, zileuton, or montelukast sodium; antibiotics (including antineoplastic antibiotics) such as vancomycin, bleomycin, pentostatin, mitoxantrone, mitomycin, dactinomycin, plicamycin, or amikacin; anticancer agents (including antineoplastic agents) such as paclitaxel, docetaxel, camptothecin or its analogues and derivatives (e.g., 9-aminocamptothecin, 9-nitrocamptothecin, 10-hydroxy-camptothecin, irinotecan, topotecan, 20-O-β-glucopyranosyl camptothecin), taxanes (e.g., baccatins, cephalomannine or their derivatives), carboplatin, cisplatin, interferon-oc$_{2A}$, interferon-$_{2B}$, interferon-α$_{N3}$ and other agents of the interferon family, levamisole, altretamine, cladribine, bovine-calmetteguerin (BCG), aldesleukin, tretinoin, procarbazine, dacarbazine, gemcitabine, mitotane, asparaginase, porfimer, mesna, amifostine, mitotic inhibitors including podophyllotoxin derivatives such as teniposide or etoposide, vinca alkaloids such as vinorelbine, vincristine, or vinblastine; topoimerase inhibitors such as camptothecin, anthraquinones, anthracyclines, teniposide, etoposide, topotecan, or irinotecan; aromatase inhibitors such as anastrozole or letrozole; GnRH inhibitors and other hormonolytics such as leuprolide, goserelin, chlorotrianisene, dinestrol, or diethylstilbestrol; antiestrogens such as tamoxifen, clomiphene, or raloxifene; antiandrogens such as bicalutamide, flutamide, hydroxyflutamide, zanoterine, or nilutamide; steroids including progestogens such as flurogestone acetate, hydroxyprogesterone, hydroxyprogesterone acetate, hydroxyprogesterone caproate, medroxyprogesterone acetate, megestrol, norethindrone, norethindrone acetate, norethisterone, norethynodrel, desogestrel, 3-keto desogestrel, gestadene, or levonorgestrel; estrogens such as estradiol and its esters (e.g., estradiol benzoate, valerate, cyprionate, decanoate and acetate), ethynyl estradiol, estriol, estrone, mestranol, or polyestradiol phosphate; corticosteroids such as betamethasone, betamethasone acetate, cortisone, hydrocortisone, hydrocortisone acetate, corticosterone, fluocinolone acetonide, flunisolide, fluticasone, prednisolone, prednisone, or triamcinolone; androgens and anabolic agents such as aldosterone, androsterone, testosterone, or methyl testosterone; antifungals such as amphotericin B, imidazoles, triazoles, or griesofulvin; herbal agents such as melatonin; lipid-soluble vitamins such as tocopherols, or retinols; and peptide drugs such as leuprolide, somatostatin, oxytocin, calcitonin, or insulin.

In certain embodiments, the at least one API is a non-opioid analgesic such as acetaminophen, ibuprofen, naproxen, diclofenac, flurbiprofen, ketoprofen, piroxicam, indomethacin, sulindac, tolmetin, meclofenamate, mefenamic acid, etodolac, ketorolac, bromfenac, celecoxib, or rofecoxib. In other embodiments, the at least one API is an opioid analgesic such as hydrocodone, hydromorphone, levorphanol, oxycodone, oxymorphone, codeine, morphine, alfentanil, fentanyl, meperidine, or sufentanil. In specific embodiments, the API is acetaminophen.

The amount of the API present in the composition can and will vary depending upon the identity of the API and the desired dosage of the API. In general, the amount of the API present in the composition ranges from about 50% to about 95% by weight of the composition. In some embodiments, the amount of the API present in the composition may range from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, or from about 90% to about 95% by weight of the composition. In certain embodiments, the amount of the API present in the composition may range from about 85% to about 95% by weight of the composition. In specific embodiments, the amount of the API present in the composition may be about 90% by weight of the composition.

(b) Surfactant System

The composition also comprises a surfactant system comprising at least one nonionic surfactant, at least one zwitterionic surfactant, or a combination thereof. The surfactant system may comprise various combinations of nonionic and/or zwitterionic surfactants. In some embodiments, the surfactant system may comprise one or more nonionic surfactants. In other embodiments, the surfactant system may comprise one or more zwitterionic surfactants. In further embodiments, the surfactant system may comprise a combination of one or more nonionic surfactants and one or more zwitterionic surfactants.

A variety of nonionic and/or zwitterionic surfactants may be included in the surfactant system. Non-limiting examples of suitable nonionic surfactants include sorbitan esters such sorbitan (Span 20), sorbitan monopalmitate (Span 40), sorbitan monostearate (Span 60), sorbitan monooleate (Span 80), sorbitan sesquioleate (Span 83), sorbitan trioleate (Span 85), sorbitan isostearate (Span 120), or combinations thereof; polyethoxylated sorbitan esters such as polyoxyethylene (20) sorbitan monolaurate (Tween 20), polyoxyethylene (4) sorbitan monolaurate (Tween 21), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), or combinations thereof; polyglycerol esters of fatty acids such as triglycerol monolaurate, triglycerol monooleate, triglycerol monostearate, polyglycerol oleate, polyglycerol, laurate, polyglycerol stearate, polyglycerol polyricinoleate, and so forth; and other nonionic surfactants such as glyceryl monolaurate, glyceryl monooleate, glyceryl monostearate, glycol distearate, glycol stearate, ceteareth-20, cetearyl glycoside, ceteth-2, ceteth-10, ceteth-20, cocamide MEA, isoceteth-20, isostearteh-20, laureth-4, laureth-23, methyl glucose sesquistearate, oleth-2, oleth-10, oleth-20, PEG-100 stearate, PEG-20 almond glycerides, PEG-60 almond glycerides, PEG-20 methyl glucose sesquistearate, PEG-7 hydrogenated castor oil, PEG-25 hydrogenated castor oil, PEG-35 hydrogenated castor oil, PEG-40 hydrogenated castor oil, PEG-60 hydrogenated castor oil, PEG-200 hydrogenated glyceryl palmate, PEG-30 dipolyhydroxystearate, PEG-4 dilaurate, PEG-40 sorbitan peroleate, PEG-7 olivate, PEG-7 glyceryl cocoate, PEG-8 dioleate, PEG-8 laurate, PEG-8 oleate, PEG-80 sorbitan laurate, PEG-40 stearate, propylene glycol isostearate, stearamide MEA, steareth-2, steareth-20, steareth-21, steareth-100, polyoxyethylene (7-8) p-t-octyl phenol (Triton X-114), polyoxyethylene (9-10) p-t-octyl phenol (Triton X-100), polyoxyethylene (9-10) nonylphenol (Triton N-101), polyoxyethylene (9) p-t-octyl phenol (Nonidet P-40), polyoxyethylene (10) cetyl ether (Brij 56), polyoxyethylene (20) cetyl ether (Brij 58), polyoxyethyleneglycol dodecyl ether (Brij 35), copolymers of ethylene oxide and propylene oxide (e.g., Pluronic F-68, Pluronic F-127, etc.), dimethyldecylphosphine oxide (APO-10), dimethyldodecylphosphine oxide (APO-12), cyclohexyl-n-ethyl-β-D-maltoside, cyclohexyl-n-hexyl-β-D-maltoside, cyclohexyl-n-methyl-β-maltoside, n-decanoylsucrose, n-decyl-β-D-glucopyranoside, n-decyl-β-maltopyranoside, n-decyl-β-D-thiomaltoside, n-dodecanoyl sucrose, decaethylene glycol monododecyl ether, N-decanoyl-N-methylglucamine, n-decyl α-D-glucopyranoside, decyl β-D-maltopyranoside, n-dodecanoyl-N-methylglucamide, n-dodecyl α-D-maltoside, n-dodecyl β-D-maltoside, heptane-1,2,3-triol, heptaethylene glycol monodecyl ether, heptaethylene glycol monododecyl ether, heptaethylene glycol monotetradecyl ether, n-hexadecyl β-D-maltoside, hexaethylene glycol monododecyl ether, hexaethylene glycol monohexadecyl ether, hexaethylene glycol monooctadecyl ether, hexaethylene glycol monotetradecyl ether, methyl-6-O-(N-heptylcarbamoyl)-α-D-glucopyranoside, nonaethylene glycol monododecyl ether, N-nonanoyl-N-methylglucamine, N-nonanoyl-N-methylglucamine, octaethylene glycol monodecyl ether, octaethylene glycol monododecyl ether, octaethylene glycol monohexadecyl ether, octaethylene glycol monooctadecyl ether, octaethylene glycol monotetradecyl ether, octyl-β-glucoside, octyl-β-thioglucoside, octyl-β-D-glucopyranoside, octyl-β-D-1-thioglucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether, polyoxyethylene (10) tridecyl ether, polyoxyethylene (100) stearate, polyoxyethylene (20) isohexadecyl ether, polyoxyethylene (20) oleyl ether, polyoxyethylene (40) stearate, polyoxyethylene (50) stearate, polyoxyethylene (8) stearate, polyoxyethylene bis(imidazolyl carbonyl), polyoxyethylene (25) propylene glycol stearate, saponin from Quillaja bark, tetradecyl-β-D-maltoside, tetraethylene glycol monodecyl ether, tetraethylene glycol monododecyl ether, tetraethylene glycol monotetradecyl ether, triethylene glycol monodecyl ether, triethylene glycol monododecyl ether, triethylene glycol monohexadecyl ether, triethylene glycol monooctyl ether, triethylene glycol monotetradecyl ether, tyloxapol, n-undecyl β-D-glucopyranoside, octylphenoxypolyethoxyethanol (IGEPAL CA-630), polyoxyethylene (5) nonylphenylether (IGEPAL CO-520), polyoxyethylene (150) dinonylphenyl ether (IGEPAL DM-970), or combinations thereof. In specific embodiments, the nonionic surfactant may be a sorbitan ester, a polyethoxylated sorbitan ester, a polyglycerol ester of a fatty acid, or combinations thereof.

Examples of suitable zwitterionic surfactants include, without limit, lecithins (e.g., a lecithin extracted from soybeans, eggs, milk, marine sources, rapeseed, cottonseed, sunflower, and the like), hydrolyzed lecithins, hydrogenated lecithins, acetylated lecithins, 3-[(3-cholamidopropyl)dimethylammonio]-2-hydroxy-1-propanesulfonate (CHAPSO), 3-[(3-cholamidopropyl)dimethylammonio]-1-propanesulfonate (CHAPS), 3-(4-heptyl)phenyl-3-hydroxypropyl) dimethylammoniopropanesulfonate (C7BzO), 3-(N,N-dimethyloctylammonio)propanesulfonate inner salt (SB3-8), 3-(decyldimethylammonio)propanesulfonate inner salt (SB3-10), 3-(dodecyldimethylammonio)propanesulfonate inner salt (SB3-12), 3-(N,N-dimethyltetradecylammonio) propanesulfonate (SB3-14), 3-(N,N-dimethylpalmitylammonio)propanesulfonate (SB3-16), 3-(N,N-dimethyloctadecylammonio)propanesulfonate (SB3-18), 3-[N,N-dimethyl(3-myristoylaminopropyl)ammonio] propanesulfonate (ASB-14), caprylyl sulfobetaine, capric amidopropyl betaine, capryloamidopropyl betaine, cetyl betaine, cocamidopropyl betaine, C12-14 alkyl dimethyl betaine, cocamidopropyl dimethylaminohydroxypropyl hydrolyzed collagen, N-[3-cocamido)-propyl]-N,N-dimethyl betaine, cocamidopropyl hydroxysultaine, cocamidopropyl sulfobetaine, cocaminobutyric acid, cocaminopropionic acid, cocoamphodipropionic acid, coco-betaine, cocodimethylammonium-3-sulfopropylbetaine, cocoiminodiglycinate, cocoiminodipropionate, coco/oleamidopropyl betaine, cocoyl sarcosinamide DEA, DEA-cocoamphodipropionate, dihydroxyethyl tallow glycinate, dimethicone propyl PG-betaine, N,N-dimethyl-N-lauric acid-amidopropyl-N-(3-sulfopropyl)-ammonium betaine, N,N-dimethyl-N-myristyl-N-(3-sulfopropyl)-ammonium betaine, N,N-dimethyl-N-palmityl-N-(3-sulfopropyl)-ammonium betaine, N,N-dimethyl-N-stearamidopropyl-N-(3-sulfopropyl)-ammonium betaine, N,N-dimethyl-N-stearyl-N-(3-sulfopropyl)-ammonium betaine, N,N-dimethyl-N-tallow-N-(3-sulfopropyl)-ammonium betaine, disodium caproamphodiacetate, disodium caproamphodipropionate, disodium caprylamphodiacetate, disodium capryloamphodipropionate, disodium cocoamphodiacetate, disodium cocoamphodipropionate, disodium isostearoamphodipropionate, disodium laureth-5 carboxyamphodiacetate, disodium lauriminodipropionate, disodium lauroamphodiacetate, disodium lauroamphodipropionate, disodium octyl b-iminodipropionate, disodium oleoamphodiacetate, disodium oleoamphodipropionate, disodium PPG-2-isodeceth-7 carboxyamphodiacetate, disodium stearoamphodiacetate, N,N-distearyl-N-methyl-N-(3-sulfopropyl)-ammonium betaine, ethylhexyl dipropionate, ethyl hydroxymethyl oleyl oxazoline, ethyl PEG-15 cocamine sulfate, isostearamidopropyl betaine, lauramidopropyl betaine, lauramidopropyl dimethyl betaine, lauraminopropionic acid, lauroamphodipropionic acid, lauroyl lysine, lauryl betaine, lauryl hydroxysultaine, lauryl sultaine; linoleamidopropyl betaine, lysolecithin, myristamidopropyl betaine, octyl dipropionate, octyliminodipropionate, oleamidopropyl betaine, oleyl betaine, 4,4(5H)-oxazoledimethanol, palmitamidopropyl betaine, palmitamine oxide, ricinoleamidopropyl betaine, ricinoleamidopropyl betaine/IPDI copolymer, sesamidopropyl betaine, sodium C12-15 alkoxypropyl iminodipropionate, sodium caproamphoacetate, sodium capryloamphoacetate, sodium capryloamphohydroxypropyl sulfonate, sodium capryloamphopropionate, sodium cocaminopropionate, sodium cocoamphoacetate, sodium cocoamphohydroxypropyl sulfonate, sodium cocoamphopropionate, sodium dicarboxyethyl cocophosphoethyl imidazoline, sodium isostearoamphopropionate, sodium lauriminodipropionate, sodium lauroamphoacetate, sodium oleoamphohydroxypropylsulfonate, sodium oleoamphopropionate, sodium stearoamphoacetate, sodium tallamphopropionate, soyamidopropyl betaine, stearyl betaine, trisodium lauroampho PG-acetate phosphate chloride, undecylenamidopropyl betaine, or combinations thereof. In certain embodiments, the zwitterionic surfactant may be a lecithin.

In specific embodiments, the surfactant system may comprise a sorbitan ester (i.e., Span), a polyethoxylated sorbitan ester (i.e., Tween), a polyglycerol ester of a fatty acid, a lecithin, or a combination thereof. In one iteration, the surfactant system may comprise a sorbitan ester and a lecithin. In another iteration, the surfactant system may comprise a sorbitan ester, a polyethoxylated sorbitan ester, and a lecithin. In yet another iteration, the surfactant system may comprise a polyethoxylated sorbitan ester, a polyglycerol ester of a fatty acid, and a lecithin.

Nonionic and zwitterionic surfactants can be classified according to the relationship (balance) between the hydrophilic portion of the compound to the lipophilic portion of the compound. This relationship is termed the hydrophile-lipophile balance or HLB. HLB values range from 0 to 20. The lower the HLB value, the more lipohilic or oil soluble the surfactant is, and the higher the HLB value, the more hydrophilic or water soluble the surfactant is.

The surfactant system included in the composition comprises one or more surfactants that are chosen such that the surfactant system has a particular HLB value. In general, the surfactant system has an HLB value ranging from about 1.0 to about 19.0. In certain embodiments, the HLB value of the surfactant system may range from about 1.0 to about 2.0, from about 2.0 to about 3.0, from about 3.0 to about 4.0, from about 4.0 to about 5.0, from about 5.0 to about 6.0, from about 6.0 to about 7.0, from about 7.0 to about 8.0, from about 8.0 to about 9.0, from about 9.0 to about 10.0, from about 10.0 to about 11.0, from about 11.0 to about 12.0, from about 12.0 to about 13.0, from about 13.0 to about 14.0, from about 14.0 to about 15.0, from about 15.0 to about 16.0, from about 16.0 to about 17.0, from about 17.0 to about 18.0, or from about 18.0 to about 19.0. In specific embodiments, the HLB value of the surfactant system may range from about 4 to about 12.

Typically, the surfactant system may comprise two or more surfactants. The HLB value of the surfactant system depends upon the HLB value of each surfactant and the concentration of each surfactant in the surfactant system. For example, a surfactant system having an HLB value of about 5.5 may contain 75% of Span 80 (HLB=4.3) and 25% of lecithin (HLB=9.1). Alternatively, a surfactant system having an HLB value of about 10 may contain 46% of Span 80 (HLB=4.3) and 54% of Tween 80 (HLB=15.0). Those skilled in the art appreciate that numerous combinations are possible to arrive at the desired HLB value.

The amount of the surfactant system present in the composition can and will vary depending upon, for example, the identity of the API, the identity and/or the amount of the excipient(s) present, and/or the desired dissolution profile. In general, the amount of the surfactant system present in the composition may range from about 0.05% to about 5.0% by weight of the composition. In various embodiments, the amount of the surfactant system present in the composition may range from about 0.05% to about 0.5%, from about 0.5% to about 1.0%, from about 1.0% to about 1.5%, from about 1.5% to about 2.0%, from about 2.0% to about 2.5%, from about 2.5% to about 3.0%, from about 3.0% to about 3.5%, from about 3.5% to about 4.0%, from about 4.0% to about 4.5%, or from about 4.5% to about 5.0% by weight of the composition. In certain embodiments, the amount of the surfactant system present in the composition may range from about 0.1% to about 3.0%. In specific embodiments the amount of the surfactant system present in the composition may range from about 0.1% to about 1.0% by weight of the composition, from about 1.0% to about 2.0% by weight of the composition, or from about 2.0% to about 3.0% by weight of the composition.

(c) Excipients

The composition also comprises at least one excipient. Suitable excipients include, without limit, binders, disintegrants, lubricants, fillers or diluents, buffering or pH modifying agents, preservatives, coloring agents, and flavoring agents. In some embodiments, the at least one excipient comprises at least one binder, at least one disintegrant, at least one lubricant, or combinations thereof. In other embodiments, the at least one excipient comprises a combination of at least one binder, at least one disintegrant, and at least one lubricant. In still other embodiments, the at least one excipient consists of a combination of at least one binder, at least one disintegrant, and at least one lubricant.

Non-limiting examples of suitable binders include starches (e.g., corn starch, potato starch, wheat starch, rice starch, and the like), pregelatinized starch, hydrolyzed starch, polyvinylpyrrolidinone (also called copovidone), polyethylene oxide, polyvinyl alcohols, C12-C18 fatty acid alcohols, polyols (e.g., maltitol, sorbitol, xylitol, polyethylene glycol, and so forth), gelatin, cellulose, methylcellulose, ethylcellulose, hydroxypropylcellulose, hydroxypropylmethylcellulose, sodium carboxymethylcellulose, lactose, pectins, alginates (e.g., alginic acid, alginate, sodium alginate, and so forth), gums (e.g., gum arabic, guar gum, gellan gum, xanthan gum, and the like), waxes (e.g., candelilla wax, carnauba wax, beeswax, and so forth), or combinations of any of the forgoing. In specific embodiments, the binder may be pregelatinized starch, polyvinylpyrrolidinone (PVP), or a combination thereof.

In some embodiments, the binder present in the composition is other than a cellulose ether. Cellulose ethers are derivatives of cellulose in which some hydroxyl groups are converted to alkyoxy groups. In such embodiments, for example, the binder is other than methylcellulose, ethylcellulose, hydroxypropylcellulose, or hydroxypropylmethylcellulose.

Examples of suitable disintegrants include, without limit, crospovidone, croscarmellose sodium, sodium carboxymethylcellulose, carboxymethylcellulose calcium, sodium starch glycolate, cellulose, microcrystalline cellulose, methylcellulose, silicon dioxide (also called colloidal silicone dioxide), alginates (e.g., alginic acid, alginate, sodium alginate, and so forth), clays (e.g., bentonite), or combinations of any of the foregoing. In specific embodiments, the disintegrant may be crospovidone, croscarmellose sodium, sodium starch glycolate, or a combination thereof. In one embodiment, the disintegrant may be crospovidone. In another embodiment, the disintegrant may be a combination of crospovidone and croscarmellose sodium. In still another embodiment, the disintegrant may be sodium starch glycolate.

Non-limiting examples of suitable lubricants include stearic acid, magnesium stearate, sodium lauryl sulfate, calcium stearate, zinc stearate, magnesium trisilicate, glyceryl behenate, sodium stearoyl fumarate, polaxamers, polyethylene glycol, talc, or combinations thereof. In certain embodiments, the lubricant may be stearic acid, magnesium stearate, sodium lauryl sulfate, or a combination thereof. In one embodiment, the lubricant may be stearic acid. In another embodiment, the lubricant may be a combination of magnesium stearate and sodium lauryl sulfate.

In some embodiments, the composition comprises at least one binder, at least one disintegrant, at least one lubricant, and further at least one additional excipient. The at least one additional excipient may be a filler or diluent, a buffering or pH modifying agent, a preservative, a coloring agent, a flavoring agent, or combinations thereof.

Non-limiting examples of suitable fillers or diluents include calcium carbonate, calcium phosphate, calcium sulfate, calcium silicate, magnesium carbonate, magnesium oxide, sodium chloride, starch, modified starches, cellulose, microcrystalline cellulose, sucrose, lactose, dextrose, mannitol, sorbitol, talc, or combinations thereof. Examples of suitable buffering or pH modifying agents include, without limit, disodium hydrogen phosphate, potassium bicarbonate, potassium carbonate, sodium bicarbonate, sodium carbonate, sodium citrate dihydrate, Tris buffered saline, phosphate buffered saline, citric acid, phosphoric acid, succinic acid, or combinations thereof. Non limiting examples of suitable preservatives include antimicrobials (such as benzyl alcohol, cetylpryidine chloride, glycerine, parabens, propylene glycol, potassium sorbate, sodium benzoate, sorbic acid, sodium propionate, and the like), antioxidants (such as alpha-tocopherol, ascorbate, butylated hydroxytoluene, and so forth), or combinations thereof. Suitable coloring agents include, but at not limited to, food, drug and cosmetic colors (FD&C), drug and cosmetic colors (D&C), or external drug and cosmetic colors (Ext. D&C). Examples of suitable flavoring agents include synthetic flavor oils and flavoring aromatics and/or natural oils, extracts from plants, leaves, flowers, fruits; sweeteners (e.g., glucose (corn syrup), dextrose, invert sugar, fructose, sugar alcohols, aspartame, stevia-derived sweeteners, sucralose, acesulfame-K, and so forth), taste-masking agents (e.g., cellulose ethers, polyvinyl alcohol and polyethylene glycol co-polymers, monoglycerides or triglycerides, polyethylene glycols, acrylic polymers, mixtures of acrylic polymers with cellulose ethers, cellulose acetate phthalate, and the like), or combinations thereof.

The amount of the at least one excipient present in the composition can and will vary depending upon, for example, the identity of the API and the desired dissolution profile of the composition. In general, the amount of the excipient(s) present in the composition will range from about 1% to about 50% by weight of the composition. In various embodiment, the amount of the excipient(s) present in the composition may range from about 1% to about 5%, from about 5% to about 10%, from about 10% to about 15%, from about 15% to about 20%, from about 20% to about 30%, from about 30% to about 40%, or from about 40% to about 50% by weight of the composition. In specific embodiments, the amount of the excipient(s) present in the composition may range from about 2% to about 25% by weight of the composition, or from about 3% to about 15% by weight of the composition.

In embodiments in which the excipient comprises at least one binder, the amount of binder present in the composition may range from about 1% to about 20% by weight of the composition. In certain embodiments, the amount of binder present in the composition may range from about 1% to about 2%, from about 2% to about 4%, from about 4% to about 6%, from about 6% to about 8%, from about 8% to about 10%, from about 10% to about 15%, or from about 15% to about 20% by weight of the composition. In specific embodiments, the amount of binder present in the composition may range from about 1% to about 10% by weight of the composition.

In embodiments in which the excipient comprises at least one disintegrant, the amount of disintegrant present in the composition may range from about 1% to about 20% by weight of the composition. In certain embodiments, the amount of disintegrant present in the composition may range from about 1% to about 2%, from about 2% to about 4%, from about 4% to about 6%, from about 6% to about 8%, from about 8% to about 10%, from about 10% to about 15%, or from about 15% to about 20% by weight of the composition. In specific embodiments, the amount of disintegrant present in the composition may range from about 1% to about 10% by weight of the composition.

In embodiments in which the excipient comprises at least one lubricant, the amount of lubricant present in the composition may range from about 0.1% to about 5% by weight of the composition. In certain embodiments, the amount of lubricant present in the composition may range from about 0.1% to about 0.5%, from about 0.5% to about 1.0%, from about 1.0% to about 1.5%, from about 1.5% to about 2.0%, from about 2% to about 3%, from about 3% to about 4%, or from about 4% to about 5% by weight of the composition. In specific embodiments, the amount of lubricant present in the composition may be about 1.0% or less by weight of the composition.

(d) Optional Ionic Surfactant

In some embodiments, the composition may further comprise at least one ionic surfactant. The optional ionic surfactant may be an anionic surfactant or a cationic surfactant.

Non-limiting examples of suitable anionic surfactants include amine dodecylbenzene sulfonate; ammonium capryleth sulfate; ammonium cumenesulfonate; ammonium di hydroxy stearate; ammonium dodecylbenzene sulfonate; ammonium laureth sulfate; ammonium laureth-12 sulfate; ammonium laureth-30 sulfate; ammonium lauryl sarcosinate; ammonium lauryl sulfate; ammonium lauryl sulfosuccinate; ammonium lignosulfonate; ammonium myreth sulfate; ammonium naphthalene sulfonate; ammonium nonoxynol-20 sulfate; ammonium nonoxynol-30 sulfate; ammonium nonoxynol-4 sulfate; ammonium nonoxynol-6 sulfate; ammonium nonoxynol-9 sulfate; ammonium oleic sulfate; ammonium perfluorooctanoate; ammonium stearate;

ammonium xylenesulfonate; butyl naphthalene sulfonate; butyl phosphate; calcium dodecylbenzene sulfonate; calcium stearoyl lactylate; calcium tetrapropylenebenzene sulfonate; capryleth-9 carboxylic acid; cetyl phosphate; cumene sulfonic acid; DEA-cetyl phosphate; DEA-dodecylbenzene sulfonate; DEA-lauryl sulfate; deceth-4 phosphate; diammonium lauryl sulfosuccinate; diammonium stearyl sulfosuccinamate; diamyl sodium sulfosuccinate; dicyclohexyl sodium sulfosuccinate; dihexyl sodium sulfosuccinate; diisobutyl sodium sulfosuccinate; dilaureth-7 citrate; dimethiconol; dinonoxynol-4 phosphate; dioctyl ammonium sulfosuccinate; dioctyl sodium sulfosuccinate; disodium cetearyl sulfosuccinamate; disodium cocamido MEA-sulfosuccinate; disodium cocamido PEG-3 sulfosuccinate; disodium deceth-6 sulfosuccinate; disodium decyl diphenyl ether disulfonate; disodium dodecyloxy propyl sulfosuccinamate; disodium isodecyl sulfosuccinate; disodium laneth-5 sulfosuccinate; disodium lauramido DEA-sulfosuccinate; disodium lauramido MEA-sulfosuccinate; disodium laureth sulfosuccinate; disodium lauryl sulfosuccinate; disodium myristamido MEA-sulfosuccinate; disodium oleamido MEA-sulfosuccinate; disodium oleamido PEG-2 sulfosuccinate; disodium oleth-3 sulfosuccinate; disodium PEG-4 cocamido MIPA sulfosuccinate; disodium ricinoleamido MEA-sulfosuccinate; disodium stearyl sulfosuccinamate; disodium undecylenamido MEA-sulfosuccinate; ditridecyl sodium sulfosuccinate; dodecenylsuccinic anhydride; dodecyl diphenyl ether disulfonic acid; dodecyl diphenyloxide disulfonic acid; dodecylbenzenesulfonic acid; glyceryl dioleate SE; glyceryl distearate SE; glyceryl ricinoleate SE; glyceryl stearate citrate; glyceryl stearate SE; glycol stearate SE; hexyl phosphate; isopropyl phosphate; isopropylamine dodecylbenzenesulfonate; isosteareth-2 phosphate; isotrideceth-3 phosphate; isotrideceth-6 phosphate; laureth-1 phosphate; laureth-12 carboxylic acid; laureth-3 phosphate; laureth-4 phosphate; laureth-6 phosphate; laureth-7 citrate; laureth-9 phosphate; lauryl phosphate; lithium lauryl sulfate; magnesium laureth sulfate; magnesium PEG-3 cocamide sulfate; MEA-laureth phosphate; MEA-lauryl sulfate; MIPA-laureth sulfate; MIPA-lauryl sulfate; myristoyl sarcosine; naphthalene-formaldehyde sulfonate; nonoxynol-10 phosphate; nonoxynol-12 phosphate; nonoxynol-3 phosphate; nonoxynol-4 phosphate; nonoxynol-4 sulfate; nonoxynol-6 phosphate; nonoxynol-7 phosphate; nonoxynol-8 phosphate; nonoxynol-9 phosphate; nonyl nonoxynol-10 phosphate; nonyl nonoxynol-15 phosphate; nonyl nonoxynol-7 phosphate; oleth-10 carboxylic acid; oleth-10 phosphate; oleth-3 carboxylic acid; oleth-4 phosphate; oleth-5 phosphate; oleth-6 carboxylic acid; oleth-7 phosphate; PEG-9 stearamide carboxylic acid; potassium cetyl phosphate; potassium deceth-4 phosphate; potassium dodecylbenzene sulfonate; potassium isosteareth-2 phosphate; potassium lauroyl sarcosinate; potassium lauryl sulfate; potassium oleate; potassium oleic sulfate; potassium perfluorooctoate; potassium ricinoleic sulfate; sodium 2-ethylhexyl phosphate; sodium 2-ethylhexyl sulfate; sodium olefin sulfonate; sodium allyloxy hydroxypropyl sulfonate; sodium behenoyl lactylate; sodium butoxyethoxy acetate; sodium butyl naphthalene sulfonate; sodium butyl oleate sulfate; sodium butyl oleate sulfonate; sodium butyl phosphate; sodium caproyl lactylate; sodium caprylyl sulfonate; sodium cetyl sulfate; sodium cholate; sodium cumenesulfonate; sodium deceth sulfate; sodium decyl diphenyl ether sulfonate; sodium decyl sulfate; sodium deoxycholate; sodium dibutyl naphthalene sulfonate; sodium didodecylbenzene sulfonate; sodium diisooctyl sulfosuccinate; sodium diisopropyl naphthalene sulfonate; sodium dilaureth-7 citrate; sodium dinonyl sulfosuccinate; sodium dodecyl diphenyl ether disulfonate; sodium dodecyl diphenyloxide disulfonate; sodium dodecylbenzenesulfonate; sodium glyceryl trioleate sulfate; sodium hexadecyl diphenyl disulfonate; sodium hexadecyl diphenyloxide disulfonate; sodium hexyl diphenyloxide disulfonate; sodium isothionate; sodium isodecyl sulfate; sodium isooctyl sulfate; sodium isostearoyl lactylate; sodium isotrideceth-15 sulfate; sodium lactate; sodium lauramido DEA-sulfosuccinate; sodium laureth phosphate; sodium laureth sulfate; sodium laureth sulfosuccinate; sodium laureth-10 phosphate; sodium laureth-11 carboxylate; sodium laureth-12 sulfate; sodium laureth-13 acetate; sodium laureth-13 carboxylate; sodium laureth-3 carboxylate; sodium laureth-4 carboxylate; sodium laureth-4 phosphate; sodium laureth-6 carboxylate; sodium laureth-7 carboxylate; sodium laureth-7 sulfate; sodium laureth-8 sulfate; sodium lauroyl glutamate; sodium lauroyl lactylate; sodium lauroyl lactylate; sodium lauroyl methylaminopropionate; sodium lauroyl sarcosinate; sodium lauryl phosphate; sodium lauryl sulfate; sodium lauryl sulfoacetate; sodium lignate; sodium lignosulfonate; sodium methallyl sulfonate; sodium methyl lauroyl taurate; sodium methyl myristoyl taurate; sodium methyl oleoyl taurate; sodium methyl palmitoyl taurate; sodium methyl stearoyl taurate; sodium methylnaphthalenesulfonate; sodium m-nitrobenzenesulfonate; sodium myreth sulfate; sodium myristoyl glutamate; sodium myristoyl sarcosinate; sodium myristyl sulfate; sodium nonoxynol sulfate; sodium nonoxynol-10 sulfate; sodium nonoxynol-10 sulfosuccinate; sodium nonoxynol-15 sulfate; sodium nonoxynol-4 sulfate; sodium nonoxynol-5 sulfate; sodium nonoxynol-6 phosphate; sodium nonoxynol-6 sulfate; sodium nonoxynol-8 sulfate; sodium nonoxynol-9 phosphate; sodium nonoxynol-9 sulfate; sodium octoxynol-2 ethane sulfonate; sodium octoxynol-3 sulfate; sodium octyl sulfate; sodium octylphenoxyethoxyethyl sulfonate; sodium oleic sulfate; sodium oleth-7 phosphate; sodium oleyl phosphate; sodium oleyl sulfate; sodium oleyl sulfosuccinamate; sodium palmitoyl sarcosinate; sodium phenyl sulfonate; sodium propyl oleate sulfate; sodium stearoyl lactylate; sodium stearyl sulfosuccinamate; sodium trideceth sulfate; sodium trideceth-3 carboxylate; sodium trideceth-6 carboxylate; sodium trideceth-7 carboxylate; sodium tridecyl sulfate; sodium tridecylbenzene sulfonate; sodium xylenesulfonate; stearoyl sarcosine; TEA-lauroyl glutamate; TEA-lauryl sulfate; tetrasodium dicarboxyethyl stearyl sulfosuccinamate; TIPA-laureth sulfate; triceteareth-4 phosphate; triceteth-5 phosphate; trideceth-2 phosphate; trideceth-3 phosphate; trideceth-5 phosphate; tridecyl phosphate; trilaureth-4 phosphate; trioctyl phosphate, or combinations thereof.

Examples of suitable cationic surfactants include, without limit, alkyltrimethylammonium bromide; benzalkonium chloride; benzalkonium chloride; benzyldimethylhexadecylammonium chloride; benzyldimethyltetradecylammonium chloride; benzyldodecyldimethylammonium bromide; benzyltrimethylammonium tetrachloroiodate; cetyltrimethylammonium bromide (CTAB); dimethyldioctadecylammonium bromide; dodecylethyldimethylammonium bromide; dodecyltrimethylammonium bromide; dodecyltrimethylammonium bromide; dodecyltrimethylammonium chloride; ethylhexadecyldimethylammonium bromide; Girard's reagent T; hexadecyltrimethylammonium bromide; hexadecyltrimethylammonium bromide; N,N',N'-polyoxyethylene(10)-N-tallow-1,3-diaminopropane; thonzonium bromide; trimethyl(tetradecyl)ammonium bromide, or combinations thereof.

The amount of the optional at least one ionic surfactant present in the composition can and will vary for a variety of reasons such as, for example, the identity of the API. In general, the amount of the optional ionic surfactant will range from about 0.01% to about 3%. In certain embodiments, the amount of optional ionic surfactant present in the composition may range from about 0.01% to about 0.03%, from about 0.03% to about 0.1%, from about 0.1% to about 0.3%, from about 0.3% to about 1.0%, from about 1.0% to about 2.0%, or from about 2.0% to about 3.0% by weight of the composition.

(e) Physical Form

The compositions disclosed herein generally are generally dry, solid compositions. As detailed below in section (II), the compositions may be prepared using spray drying technology. Thus, the compositions comprise a plurality of spray dried particles. The plurality of spray dried particles may be formed into a variety of dosage units. In some embodiments, the plurality of spray dried particles may be pressed into solid dosage units such as tablet, caplet, compact, pellet, or pill. In certain iterations, a tablet or caplet may be encased within a gelatin capsule/coating to form a geltab or gelcap, respectively. In other iterations, a caplet may be end-capped with a gelatin capsule half. In other embodiments, the plurality of spray dried particles may be enclosed in a capsule, for example a hard capsule. The shell of the capsule may comprise gelatin, hydrolyzed starch, or a polymer such as hydroxypropylmethylcellulose. In still further embodiments, the plurality of spray dried particles may be enclosed in a sachet.

In embodiments in which the dosage unit is a solid dosage unit such as a tablet, caplet, etc., the solid dosage unit may have a hardness that ranges from about 10 N to about 300 N. In specific embodiments, the solid dosage unit may have a hardness that ranges from about 20 N to about 200 N. Additionally, the solid dosage unit may have a friability of no greater than about 1.0%. In specific embodiments, the solid dosage unit may have a friability of about 0.5% or less.

In certain embodiments, the tablet, caplet, compact, pellet, or pill may comprise a coating. In some embodiments, a tablet or caplet may be encased (partially or completely) in a gelatin capsule or coated with a gelatin coating, thereby forming a geltab or gelcap, respectively. In other embodiments, the tablet or caplet, etc., may be coated with a film coating, thereby forming a coated tablet, caplet, etc. Typically, film coatings comprise at least one water-soluble polymer and at least one plasticizer. Non-limiting examples of suitable polymers include hydroxypropylmethylcellulose, hydroxypropylcellulose, hydroxypropylethylcellulose, ethylcellulose, methylcellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methyl methacrylate, polyvinyl acetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. In still other embodiments, the coating may be a water-insoluble coating such as a coating comprising methylcellulose, ethylcellulose, or another water-insoluble polymer.

(f) Dissolution Profiles

The compositions disclosed herein have different dissolution profiles. The dissolution profile is modified by adjusting the types and/or amounts the excipient(s) and the surfactant system included in the composition. Dissolution profiles or dissolution rates may be determined using standard, well-known USP in vitro dissolution tests. In some embodiments, the compositions may exhibit rapid or immediate release of the API, wherein at least about 70% of the API is released within about 10 minutes. In other embodiments, the compositions may exhibit delayed or extended release of the API, wherein no more than about 80% of the API is released within about 30 minutes.

In general, compositions comprising surfactant systems with high HLB values have slower rates of dissolution than compositions comprising surfactant systems with lower HLB values. For example, a composition comprising a surfactant system in which the calculated HLB is about 10 has a slower rate of dissolution than a composition comprising a surfactant system in which the calculated HLB is about 5.5 (see Example 1 and FIG. 1; compare Formulas O and U). The rate of dissolution, however, is also affected by the identity and/or amount of the excipients in the composition. For example, compositions in which all the components are identical except for the identity of the disintegrant (e.g., crospovidone vs. sodium starch glycolate) have different dissolution profiles (see Example 1 and FIG. 1; compare Formulas O and M). Thus, the dissolution profile of the composition may be modified by manipulating the HLB value of the surfactant system and/or modifying the identity and/or amount of the excipient(s).

In embodiments in which the composition exhibits rapid or immediate release of the API, the composition may also exhibit rapid dispersibility or disintegration of the inactive ingredients. That is, the composition completely dissolves, disperses, or disintegrates within a short period of time during in vitro dissolution tests. In some embodiments, the composition completely dissolves, disperses, or disintegrates (leaving no visible residue) within about 10 minutes, about 20 minutes, about 30 minutes, or about 60 minutes.

(g) Specific Compositions

Specific compositions may comprise acetaminophen as the API, a surfactant system comprising at least one sorbitan ester, at least one polyethoxylated sorbitan ester, at least one lecithin, at least one polyglycerol ester of a fatty acid, or combinations thereof; and the at least one excipient may comprise a binder comprising pregelatinized starch and polyvinylpyrrolidinone, a disintegrant comprising crospovidone, croscarmellose sodium, sodium starch glycolate, or combinations thereof, and a lubricant comprising stearic acid, magnesium stearate, sodium lauryl sulfate, or combinations thereof. The amount of acetaminophen present in the composition may range from about 80% to about 95% by weight of the composition, the amount of the surfactant system present in the composition may range from about 0.1% to about 3% by weight of the composition, the amount of binder present in the composition may range from about 1% to about 10% by weight of the composition, the amount of disintegrant present in the composition may range from about 1% to about 10% by weight of the composition, and the amount of lubricant present in the composition may be about 1% or less by weight of the composition. The specific compositions may comprise a plurality of spray dried particles and may have a form chosen from tablets, caplets, gelcaps, geltabs, capsules, or sachets. Moreover, the specific compositions have different dissolution profiles depending upon the identity and/or the amount of in the surfactant system and/or the at least one excipient present in the composition. As an example, the acetaminophen generally has a faster rate of dissolution when the HLB value of the surfactant system is about 4-6 than when the HLB value of the surfactant system is about 9-11.

(II) Processes for Preparing the Compositions

Another aspect of the present disclosure comprises processes for preparing the compositions detailed above in section (I). In particular, processes are provided for preparing spray dried particles of the compositions disclosed herein. The processes comprise forming an aqueous slurry by mixing into water i) at least one excipient, ii) a pharmaceutically active ingredient (API) having low aqueous solubility, and iii) a surfactant system comprising at least one nonionic surfactant and/or at least one zwitterionic surfactant. The processes further comprise spray drying the aqueous slurry to form the spray dried particles. The spray dried particles may be formed into various dosage units.

(a) Forming an Aqueous Slurry

The first step of the process comprises forming an aqueous slurry by mixing into water the components of the composition. Thus, the only solvent used in the process is water. No other solvent is used.

The process comprises forming a mixture (i.e., aqueous slurry) by adding the API, the one or more excipients, and the surfactant system to an appropriate volume of water. The API, the excipients, and the surfactant system may be added in any order. Additionally, the API, the excipients, and the surfactant system may be added individually, in pairs, or in various combinations. The surfactant system may be pre-mixed with a fraction of the water to form a surfactant dispersion. For example, the surfactant dispersion may be prepared by mixing the surfactant or combination of surfactants with a volume of water that ranges from about 1% to about 20% of the total volume of water used in the process. The surfactant dispersion may be heated to a temperature ranging from about 30° C. to about 95° C. viith or without mixing. The surfactant dispersion may be added to the aqueous mixture (which may contain the API and/or the excipients). In specific embodiments, the one or more excipients are added to the water to form a mixture, then the API is added to the mixture, and lastly a surfactant dispersion is added to the mixture, thereby forming the aqueous slurry.

The ratio of solids (i.e., excipients, API, and surfactants) to water in the aqueous slurry can and will vary depending upon a variety of factors. In general, the aqueous slurry may comprise from about 0.25 parts to about 4 parts of solids to about 1 part of water by weight. In various embodiments, the aqueous slurry may comprise from about 0.5 parts to about 1.5 parts of solids to about 1 part of water by weight. In specific embodiments, aqueous slurry may comprise about 1 part of solids to about 1 part of water by weight. Stated another way, the aqueous slurry may comprise from about 20% to about 80% of solids by weight. In certain embodiments, the aqueous slurry may comprise from about 40% to about 60% of solids by weight. In other embodiments, the aqueous slurry may comprise about 50% of solids by weight.

In general, the aliquot of water is mixed while the components of the composition are added to the water. The mixing means may be an overhead mixer, a high shear mixer, a high shear rotor stator mixer, a high viscosity mixer, a ribbon blender, a continuous processor, a cone screw blender, a planetary mixer, a double planetary mixer, a counter-rotating mixer, a double or triple shaft mixer, a paddle mixer, or a jet mixer.

The speed of the mixer or mixing unit may be varied according to the viscosity of the mixture. In general, the mixture is mixed long enough after the addition of the components, individually or collectively, to ensure formation of a uniform mixture. Typically, the mixing is performed at ambient or room temperature (and at atmospheric pressure).

(b) Spray Drying

The second step of the process comprises spray drying the aqueous solution to form the spray dried particles. Spray drying is well known to those versed in the art. In general, the process parameters are modified to produce particles having a particular average particle size and a particular moisture content. Additional guidance regarding process variables can be found, for example, in K. Masters, *Spray Drying Handbook*, $4^{th}$ edition, Halsted Press, 1985.

In general, the average particle size of the spray dried particles may range from about 10 micrometers (μm) to about 500 μm. In some embodiments, the average particle size of the spray dried particles may range from about 20 μm to about 400 μm. In specific embodiments, the average particle size of the particles may range from about 50 μm to about 250 μm. In general, the spray dried particles form a free flowing powder.

The targeted moisture content of the spray dried particles may range from about 0.2% to about 2.0%. In certain embodiments, the moisture content of the spray dried particles may range from about 0.5% to about 1.5%. In specific embodiments, the moisture content of the spray dried particles may range from about 0.7% to about 1.3%.

(c) Forming Dosage Units

Once the spray dried particles have been formed, they may be used to form dosage units, as mentioned above in section (I)(e), using standard procedures. Advantageously, the spray dried particles may be directly compressed into tablets, caplets, and the like with no intervening steps. That is, no blending, granulating, compacting, milling, or coating steps are needed prior to formation of tablets, caplets, etc. from the spray dried particles. Thus, the processes for preparing the compositions disclosed herein may be described as "drum-to-hopper" processes.

The compressive force used to form tablets, caplets, and the like can and will vary depending upon a variety of factors, such as the components of the composition and desired dissolution rate. In general, the compressive force (kN) may vary from about 5 kN to about 80 kN. In various embodiments, the compressive force may range from about 5 to about 20 kN, from about 20 to about 40 kN, or from about 40 to about 80 kN. In specific embodiments, the compressive force may range from about 15 kN to about 25 kN.

Definitions

Compounds useful in the compositions and processes include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

As used herein, an API having "low aqueous solubility" refers to an API that meets the USP definition of "sparingly soluble," "slightly soluble," "very slightly soluble," or "practically insoluble."

A hydrophile-lipophile balance (HLB) value reflects the balance between the hydrophilic portion of a nonionic or zwitterionic surfactant to the lipophilic portion of the surfactant. HLB values can range from 0 (completely lipophilic) to 20 (completely hydrophilic).

As used herein, a "solid pharmaceutical composition" refers to a composition that is other than a liquid or an emulsion. Non-limiting examples of solid compositions include powders, particles, granules, beads, pellets, tablets, caplets, geltabs, gelcaps, compacts, pills, capsules, and sachets.

As various changes could be made in the above-described compositions and processes methods without departing from the scope of the invention, it is intended that all matter contained in the above description and in the examples given below, shall be interpreted as illustrative and not in a limiting sense.

EXAMPLES

Example 1

Preparation of Acetaminophen Formulations

To determine whether the dissolution profile could be modified by varying the type and/or amount of surfactants and excipients, five different formulations were prepared. The formulations are presented in Table 1. Each formulation contained 500 mg of acetaminophen (APAP) per tablet or caplet.

TABLE 1

Formulations

Amount (as wt % in Formula)

| Component | Formula O | Formula M | Formula J2 | Formula L | Formula U |
|---|---|---|---|---|---|
| Acetaminophen | 90.00 | 90.00 | 90.00 | 90.00 | 90.00 |
| Starch 1500 | 4.90 | 4.90 | 3.08 | 4.90 | 1.15 |
| PVP | 1.25 | 1.25 | 1.22 | 1.25 | 1.25 |
| Crospovidone | — | 2.00 | 5.00 | 2.00 | 2.50 |
| Sodium Starch Glycolate | 2.00 | — | — | — | — |
| Croscarmellose Sodium (Ac-Di-Sol) | — | — | — | — | 3.8 |
| Span 80 | 0.45 | 0.45 | 0.50 | 1.00 | 0.75 |
| Tween 80 | 0.65 | 0.65 | 0.10 | 0.10 | — |
| Lecithin | 0.50 | 0.50 | 0.10 | 0.50 | 0.25 |
| Stearic Acid | 0.25 | 0.25 | — | 0.25 | 0.30 |
| Magnesium Stearate/SLS blend (Stear-O-Wet) | — | — | 0.50 | — | — |
| Total | 100.00 | 100.00 | 100.00 | 100.00 | 100.00 |
| Calculated HLB of the surfactant combination | 10.1 | 10.1 | 6.5 | 6.4 | 5.5 |

A dispersion of the surfactants was prepared by mixing Span 80 or Span 80 and Tween 80 in about one-fifth of the total volume of water to be used to make the aqueous slurry. Lecithin was added to the Span/Tween/water mixture. The mixture was heated to about 80-90° C. with moderate stirring. The mixture was stirred until a smooth dispersion was formed.

The rest of the water was added to a mixing vessel (the final slurry had about 50-60% solids by weight). Using a high shear mixer, each excipient was added to the mixing vessel while mixing to achieve a uniform slurry. Then APAP was added to the mixing vessel, and the speed of the mixer was increased as needed to maintain uniformity. Lastly, the surfactant dispersion was added to the vessel and mixing was continued for enough time to insure formation of a uniform slurry. The slurry was spray dried to form spray dried powder. Tablets were formed from the spray dried powder using a tablet press.

Example 2

In Vitro Dissolution Tests

Figure 1:
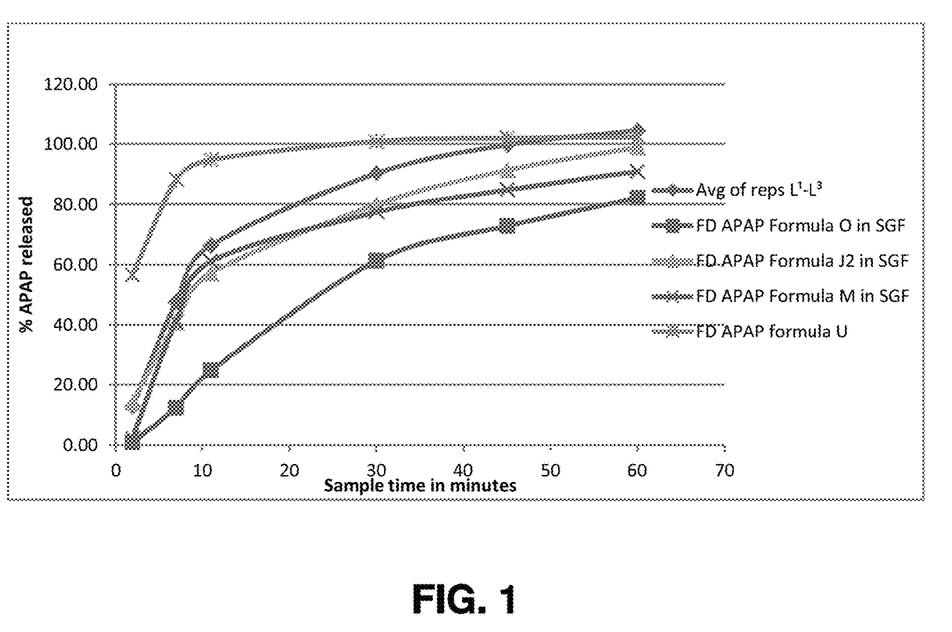
FIG. 1 diagrams the dissolution profiles of the indicated formulations. Plotted is the percent of acetaminophen (APAP) released over 60 minutes in simulated gastric fluid (SGF) using a standard USP in vitro dissolution procedure.

The in vitro dissolution of APAP from the formulations prepared in Example 1 were measured using approved USP and/or EP processes. In particular, dissolution was measured using an USP approved Type 2 paddle apparatus, at a paddle speed of 50 rpm or 100 rpm, at a constant temperature of 37±0.5° C., in simulated gastric fluid (SGF) (i.e., buffered 0.1N HCl). The amount of APAP in the dissolution fluid was determined via UV absorption at regular intervals. The dissolution profiles of the five formulations are shown in FIG. 1. Formula U, which contained a surfactant combination having an HLB of 5.5, had the fastest rate of dissolution, and Formula O, which contained a surfactant combination of 10.1, had the slowest rate of release. Maintaining the same surfactant combination and changing the identity and/or amount of some of the excipients altered the rate of dissolution (compare Formulas O and M, and Formulas L and U).

Example 3

Modification of Fast Dissolve Formulations

The ratios of the components in the fast release formulation, Formula U, were modified to make three new formulations, as shown in Table. 2. The formulations were prepared essentially as described in Example 1.

TABLE 2

Fast Dissolve Formulations

Amount (as wt % in Formula)

| Component | Formula U | Formula B-2 | Formula E-3 | Formula E-4 |
|---|---|---|---|---|
| Acetaminophen | 90.00 | 90.00 | 90.00 | 90.00 |
| Starch 1500 | 1.15 | 2.50 | 2.50 | 2.70 |
| PVP | 1.25 | 2.00 | 2.25 | 2.25 |
| Crospovidone | 2.50 | 2.50 | 2.50 | 2.50 |
| Croscarmellose Sodium (Ac-Di-Sol) | 3.8 | 2.00 | 2.00 | 2.00 |
| Span 80 | 0.75 | 0.50 | 0.30 | 0.15 |
| Lecithin | 0.25 | 0.15 | 0.10 | 0.05 |
| Stearic Acid | 0.30 | 0.30 | 0.35 | 0.35 |
| Total | 100.00 | 100.00 | 100.00 | 100.00 |

Figure 2:
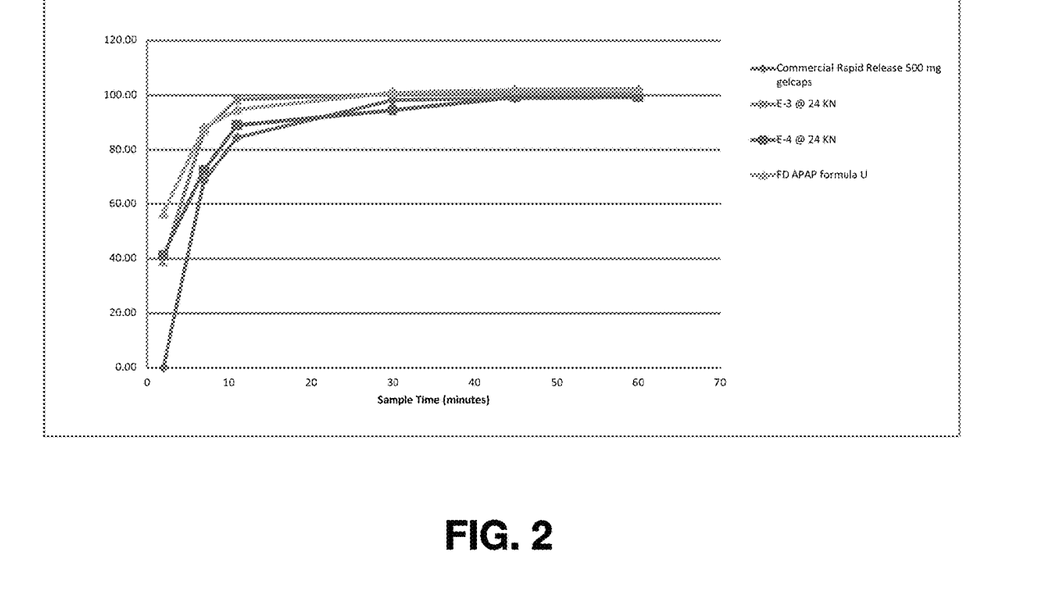
FIG. 2 presents the dissolution profiles of several rapid dissolve APAP formulations. Plotted is the percent of APAP released over 60 minutes in SGF for the indicated test formulations and a commercial APAP formulation.

The dissolution of the tablets was measured essentially as detailed above in Example 2 and compared with the dissolution of commercial rapid release APAP (500 mg) gelcaps. The results are shown in FIG. 2. The test formulations had faster dissolution profiles than the commercial formulation. For example, at 5 minutes, about 70% of APAP was released the commercial formulation, whereas about 75% or more of APAP was released from the test formulations.

Example 4

Modification of Extended Release Formulations

The components of the extended release formulations, M and O, were modified as shown in Table 3 to make three new formulations. The formulations were prepared essentially as described in Example 1.

TABLE 3

Extended Release Formulations

| | Amount (as wt % in Formula) | | | | |
|---|---|---|---|---|---|
| Component | Formula M | Formula O | Formula O3 | Formula O5 | Formula O6 |
| Acetaminophen | 90.00 | 90.00 | 90.00 | 90.00 | 90.00 |
| Starch 1500 | 4.90 | 4.90 | 4.15 | 3.15 | 4.90 |
| PVP | 1.25 | 1.25 | 1.25 | 1.25 | 1.25 |
| Crospovidone | 2.00 | — | — | — | — |
| Sodium Starch Glycolate | — | 2.00 | 2.00 | 2.00 | 2.00 |
| Span 80 | 0.45 | 0.45 | 0.45 | 0.45 | — |
| Polyglycerol Monooleate | — | — | — | — | 0.45 |
| Tween 80 | 0.65 | 0.65 | 0.65 | 0.65 | 0.65 |
| Lecithin | 0.50 | 0.50 | 0.50 | 0.50 | 0.50 |
| Stearic Acid | 0.25 | 0.25 | — | — | 0.25 |
| Magnesium Stearate/SLS blend (Stear-O-Wet) | — | — | 1.00 | 2.00 | — |
| Total | 100.00 | 100.00 | 100.00 | 100.00 | 100.00 |

Figure 3:
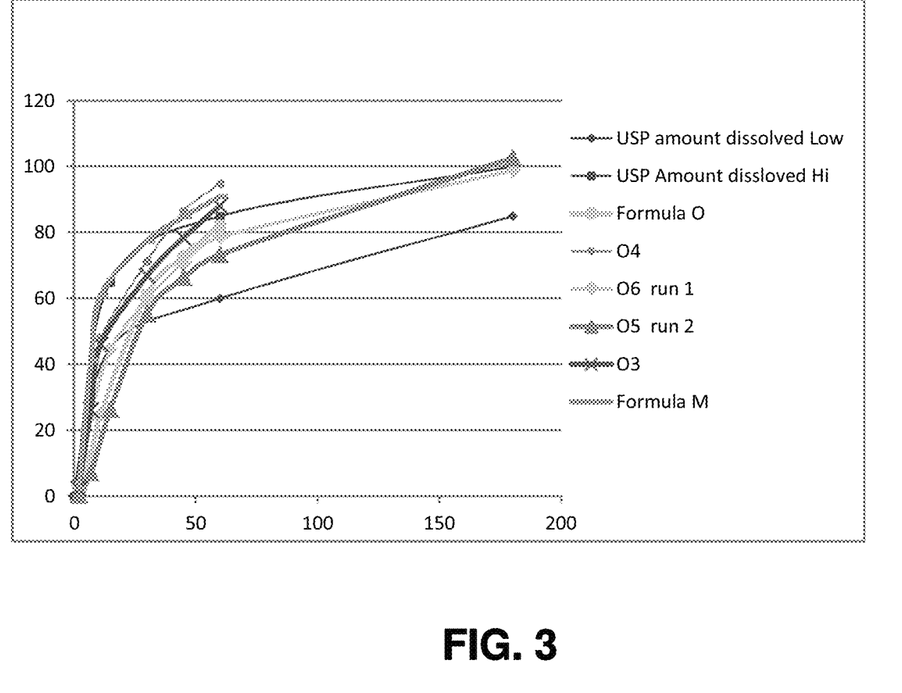
FIG. 3 shows the dissolution profiles of several extended release APAP test formulations. Plotted is the percent of APAP released over 180 minutes in SGF for the indicated test formulations. Also shown are the upper and lower specifications for the USP extended release dosage Test 1.
Figure 4:
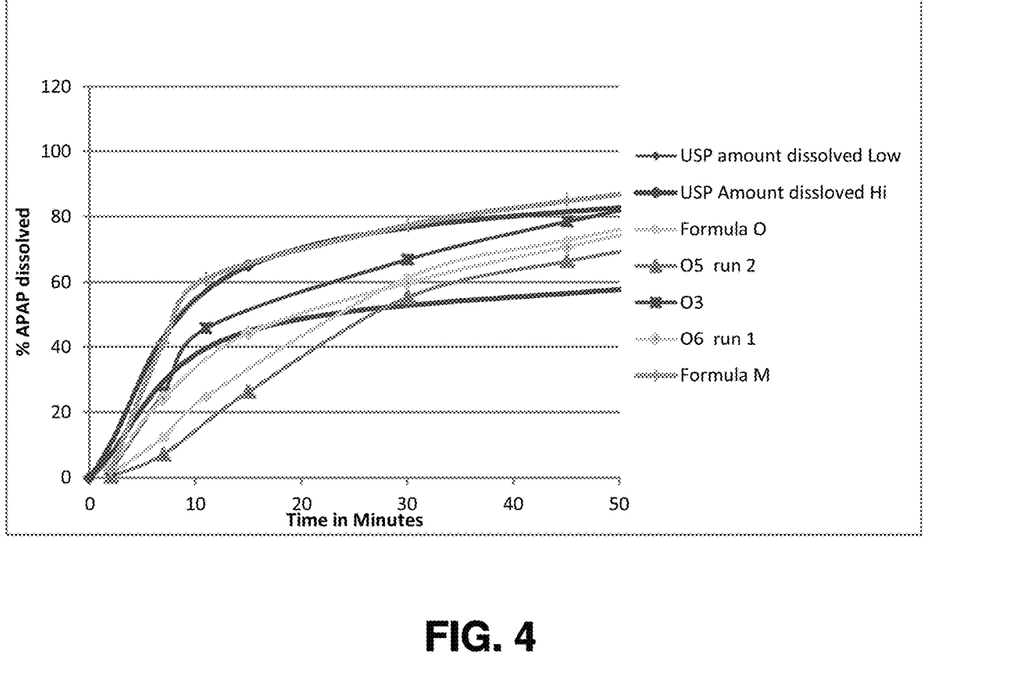
FIG. 4 presents the dissolution profiles of several extended release APAP test formulations. Plotted is the percent of APAP released during the first 60 minutes of the test for the indicated test formulations. Also shown are the upper and lower specifications for the USP extended release dosage Test 1.

The in vitro dissolution of the formulations was tested essentially as described in Example 2. The dissolution profiles over the course of 180 minutes are shown FIG. 3 and the dissolution profiles during the first 50 minutes of the test are shown in FIG. 4. Some formulations fell within the upper and lower specifications for the USP extended release dosage Test 1 during the early time points, but other formulations fell within the specified limits for the USP extended release dosage Test 1 at later time points.

What is claimed is:

1. A solid pharmaceutical composition consisting of a plurality of spray dried particles consisting of:
   90 wt% of acetaminophen;
   0.45 wt% of sorbitan monooleate or 0.45 wt% polyglycerol monooleate;
   0.65 wt% of polyoxyethylene (20) sorbitan monooleate;
   0.50 wt% of lecithin;
   2.0 wt% of crospovidone or 2.0 wt% of sodium starch glycolate;
   3.15-4.90 wt% of pregelatinized starch;
   1.25 wt% polyvinylpyrrolidinone; and
   0.25% of stearic acid or 1.0-2.0 wt% of a blend of magnesium stearate and sodium lauryl sulfate,
   wherein the solid pharmaceutical composition releases no more than 80% of the acetaminophen within 30 minutes in an in vitro dissolution test.

* * * * *